United States Patent
Allaire et al.

(10) Patent No.: US 11,051,776 B2
(45) Date of Patent: Jul. 6, 2021

(54) DEVICE AND METHOD FOR DISPLAYING IMAGE INFORMATION

(71) Applicant: KONINKLIJKE PHILIPS N.V., Eindhoven (NL)

(72) Inventors: Stéphane Allaire, Nanterre (FR); Alexandra Groth, Hamburg (DE); Juergen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 233 days.

(21) Appl. No.: 15/315,479

(22) PCT Filed: Jun. 15, 2015

(86) PCT No.: PCT/EP2015/063251
§ 371 (c)(1),
(2) Date: Dec. 1, 2016

(87) PCT Pub. No.: WO2015/197384
PCT Pub. Date: Dec. 30, 2015

(65) Prior Publication Data
US 2017/0245815 A1    Aug. 31, 2017

(30) Foreign Application Priority Data
Jun. 26, 2014 (EP) .................................. 14306006

(51) Int. Cl.
*A61B 6/00* (2006.01)
*A61B 5/055* (2006.01)
(Continued)

(52) U.S. Cl.
CPC .............. *A61B 6/466* (2013.01); *A61B 5/055* (2013.01); *A61B 5/7425* (2013.01);
(Continued)

(58) Field of Classification Search
CPC ....... A61B 6/466; A61B 6/463; A61B 8/0883; A61B 6/503; A61B 8/466; A61B 5/7425;
(Continued)

(56) References Cited

U.S. PATENT DOCUMENTS 8,454,514 B2   6/2013   Kawagishi
9,262,830 B2   2/2016   Bakker
(Continued)

FOREIGN PATENT DOCUMENTS

JP   11299782       11/1999
JP   2001087229 A   4/2001

OTHER PUBLICATIONS

Otey, M.E. et al., (2006), Automatic view recognition for cardiac ultrasound images. In MICCAI: International Workshop on Computer Vision for Intravascular and Intracardiac Imaging (pp. 187-194).
(Continued)

*Primary Examiner* — Jennifer Mehmood
*Assistant Examiner* — Kim Thanh T Tran (57) ABSTRACT

The present invention relates to a device for displaying image information, the device comprising: a detection unit (10), which is configured to identify a plurality of admissible display orientations of multiple data sets; a restriction unit (20), which is configured to restrict the plurality of admissible display orientations of at least one of the multiple data sets to a set of admissible display orientations in common for all the multiple data sets; and/or to restrict a plurality of admissible scrolling directions of at least one of the multiple data sets to a set of admissible scrolling directions that are normal to the restricted admissible display orientations; and a display unit (30), which is configured to display the multiple data sets using the set of the restricted display orientations and/or the set of restricted scrolling directions.

15 Claims, 3 Drawing Sheets

(51) Int. Cl.
　　　*A61B 5/00*　　　(2006.01)
　　　*A61B 8/00*　　　(2006.01)
　　　*G06T 19/20*　　(2011.01)
　　　*G01S 7/52*　　　(2006.01)
　　　*G01R 33/56*　　(2006.01)
　　　*A61B 8/08*　　　(2006.01)
　　　*G06T 11/60*　　(2006.01)
　　　*G06F 3/0481*　　(2013.01)
　　　*G06F 3/0485*　　(2013.01)

(52) U.S. Cl.
　　　CPC .......... *A61B 6/4417* (2013.01); *A61B 6/463* (2013.01); *A61B 6/503* (2013.01); *A61B 6/5223* (2013.01); *A61B 6/5247* (2013.01); *A61B 8/0883* (2013.01); *A61B 8/4416* (2013.01); *A61B 8/463* (2013.01); *A61B 8/466* (2013.01); *A61B 8/523* (2013.01); *A61B 8/5261* (2013.01); *G01R 33/5608* (2013.01); *G01S 7/52074* (2013.01); *G06T 11/60* (2013.01); *G06T 19/20* (2013.01); *A61B 5/7207* (2013.01); *A61B 2576/023* (2013.01); *G06F 3/0485* (2013.01); *G06F 3/04815* (2013.01); *G06T 2210/41* (2013.01); *G06T 2219/008* (2013.01); *G06T 2219/028* (2013.01); *G06T 2219/2016* (2013.01)

(58) Field of Classification Search
　　　CPC ..... A61B 6/4417; A61B 8/4416; A61B 8/463; A61B 8/5261; A61B 6/5247; A61B 8/523; A61B 6/5223; A61B 5/055; G06T 11/60; G06T 19/20; G06T 2210/41; G06T 2219/008; G06T 2219/028; G06T 2219/2016; G06F 3/0485; G06F 3/04815; G06F 3/0481; G01R 33/5608; G01S 7/52074; G16H 30/40

USPC .......................... 345/419; 600/441; 315/419
　　　See application file for complete search history.

(56) References Cited

U.S. PATENT DOCUMENTS

| | | | |
|---|---|---|---|
| 2003/0194121 A1* | 10/2003 | Eberhard | A61B 6/463 382/132 |
| 2007/0010743 A1 | 1/2007 | Arai | |
| 2008/0021301 A1* | 1/2008 | Gonzalez | G06T 7/0012 600/407 |
| 2008/0292164 A1* | 11/2008 | Azar | A61B 5/0091 382/131 |
| 2008/0298660 A1 | 12/2008 | Yamagata | |
| 2009/0054756 A1* | 2/2009 | Granger | G06T 7/0012 600/410 |
| 2009/0097723 A1 | 4/2009 | Washburn et al. | |
| 2009/0135191 A1* | 5/2009 | Azar | A61B 6/502 345/522 |
| 2009/0297006 A1* | 12/2009 | Suri | G06T 7/38 382/131 |
| 2009/0313585 A1 | 12/2009 | Hellinger et al. | |
| 2010/0239150 A1 | 9/2010 | Ishikawa et al. | |
| 2011/0178389 A1* | 7/2011 | Kumar | A61B 5/055 600/411 |
| 2012/0172700 A1* | 7/2012 | Krishnan | A61B 6/032 600/407 |
| 2012/0249549 A1 | 10/2012 | Endo et al. | |
| 2012/0262453 A1 | 10/2012 | Endo | |
| 2013/0113729 A1* | 5/2013 | Chiang | G06F 3/04883 345/173 |
| 2013/0182084 A1 | 7/2013 | Tsukagoshi et al. | |

OTHER PUBLICATIONS

Sabuncu, et al: "Graph-Theoretic Image Registration Using Prior Examples", 2005 13th European Signal Processing Conference.

* cited by examiner

DEVICE AND METHOD FOR DISPLAYING IMAGE INFORMATION

FIELD OF THE INVENTION

The present invention relates to the field of flexible and aligned displaying and viewing of two-dimensional and/or three-dimensional images and/or sequences. In particular, the present invention relates to a device and a method for displaying image information.

BACKGROUND OF THE INVENTION

US 2008/0298660 A1 describes a three-dimensional diagnostic imaging system for acquiring and displaying three-dimensional images, wherein the system includes an ultrasound diagnostic imaging apparatus configured to display any cross-section of a three-dimensional image extracted from volume data including an affected part of a subject.

WO 2011/074207 A1 describes an information processing apparatus, which includes a display control unit configured to control the displaying of a cross-sectional image along a first cross-section.

US 2009/0313585 A1 describes a method and a user interface for the presentation of multiple image data sets for a comparative evaluation, wherein a determination is made of at least three organization parameters that describe a sorting of the images within an image data set.

SUMMARY OF THE INVENTION

There may be a need to improve devices and methods for displaying image information.

These needs are met by the subject-matter of the independent claims. Further exemplary embodiments are evident from the dependent claims and the following description.

An aspect of the invention relates to a device for displaying image information, the device comprising: a detection unit, which is configured to analyze multiple data sets, which comprise a first data set with a first data set modality and a second data set with a second data set modality, providing analyzed differences of the first data set modality and the second data set modality; a restriction.

A further, second aspect of the present invention relates to a medical imaging system comprising a device according to the first aspect of the present invention or according to any embodiment of the first aspect of the present invention.

A further, third aspect of the present invention relates to a method for displaying image information, the method comprising the steps of identifying a plurality of admissible display orientations of multiple data sets; restricting the plurality of admissible display orientations of at least one of the multiple data sets to a set of admissible display orientations in common for all the multiple data sets; and/or restricting a plurality of admissible scrolling directions of at least one of the multiple data sets to a set of scrolling directions that are normal to the restricted admissible display orientations; and displaying the multiple data sets using the set of the restricted display orientations and/or the set of restricted scrolling directions.

The present invention advantageously provides a flexible aligned viewing of two-dimensional and/or three-dimensional images and/or sequences of images from different imaging modalities, a general display concept is correspondingly provided. The present invention advantageously provides a snapped viewing concept which enables to keep in sync the display of multiple aligned data sets, despite differences in the data dimensionality of the data sets.

The present invention advantageously provides that the combined displaying of three-dimensional volume data sets and data sets comprising two-dimensional slices is coordinately and synchronously maintained.

Further, the present invention advantageously provides that a combined displaying of two data sets of two-dimensional slices is provided, where the data sets are pre-aligned in space, wherein the present invention advantageously provides a restricting of the viewing orientation possibilities for multi-planar reformatting, MPR, of the data sets to only planes parallel to the two-dimensional slice or slices.

The present invention advantageously provides that the orientation possibilities of multiple views of three-dimensional or two-dimensional data are snapped to a discrete and/or sparse subset of orientations admissible for all the two-dimensional data displayed simultaneously. In other words, the orientation possibilities of multiple view of at least one of the multiple data sets are restricted to the admissible display orientation in common for all the multiple data sets.

The present invention advantageously provides that a scrolling through three-dimensional data is allowed along a normal axis with respect to the displayed two-dimensional data plane.

The present invention advantageously proposes a snapped viewing concept that allows displaying highlights of the underlying alignment of the data sets. The present invention advantageously provides a way that the observer realizes that the data sets are linked with respect to each other.

The present invention advantageously highlights into any three-dimensional volume the anatomy-specific views, for instance cardiac views that were chosen in a two-dimensional or slice-based protocol.

In other words, the combined display of a three-dimensional volume data set and a data set of two-dimensional slices, or for the combined displaying of two data sets of two-dimensional slices, a displaying and viewing mode is provided which restricts the displaying or viewing orientation possibilities for multi-planar reformatting, MPR.

The present invention can be applied in the presence of various types of limiting data sets, i.e. for which not all orientations are admissible, such as: a single two-dimensional slice, a multiple two-dimensional data set, i.e. a set of two-dimensional slices where multiple orientation views may be available, a data set with very anisotropic resolution, e.g. a stack of two-dimensional slices.

The snapped-orientation displaying or viewing mode may be automatically switched on before loading any data set and/or as soon as the limiting data set is selected to be among the data sets displayed. The orientation for immediate display may be selected as the one closest to the last orientation displayed, which can be perceived as an orientation snapping behavior of the view port.

The snapped orientation viewing mode can be automatically switched off, e.g. when two limiting data sets have incompatible admissible orientations; typically a two-dimensional data set and another two-dimensional data set recorded merely perpendicular to each other.

When scrolling parallel slices, a visual sign may highlight that use actually not only match in orientation but also match in actual position or height along the common normal, e.g. frames for a common color may be added around the aligned views to show that they are in full spatial sync. Furthermore, at mode on-switch, the position of the parallel slice for immediate display may be selected as the one closest to the position of the limiting data set view, and vice versa for an M2D data set, or simply as the position of the parallel slice that goes through the features in the last slice displayed, which can be perceived as a position snapping behavior of the view port.

According to an exemplary embodiment of the present invention, the detection unit is configured to analyze as the first data set a three-dimensional data set and as the second data set a two-dimensional data set.

According to a further embodiment of the present invention, the restriction unit is configured to restrict the plurality of admissible display orientations for the first data set to the set of restricted display orientations, which are planes parallel to the two-dimensional second data set.

According to an exemplary embodiment of the present invention, the restriction unit is configured to restrict the plurality of admissible scrolling directions for the first data set to the set of restricted scrolling directions, which are normal to displayable planes of the two-dimensional second data set.

According to an exemplary embodiment of the present invention, the detection unit is configured to identify the plurality of admissible display orientations using view classification procedures or using user input.

According to an exemplary embodiment of the present invention, the restriction unit is configured to restrict the plurality of admissible display orientations and/or the plurality of admissible scrolling directions during a viewing mode of the device.

According to an exemplary embodiment of the present invention, the restriction unit is configured to restrict the plurality of admissible display orientations for at least one of the multiple data sets to the set of restricted display orientations based on the analyzed differences within a fixed angle threshold of an admissible normal.

According to an exemplary embodiment of the present invention, the restriction unit is configured to restrict the plurality of admissible scrolling directions for at least one of the multiple data sets to the set of restricted scrolling directions based on the analyzed differences within a fixed angle threshold of an admissible normal.

According to an exemplary embodiment of the present invention, the display unit is configured to display a position matching of the multiple data sets, when multiple data sets are displayed by the display unit and a scrolling through at least one of the multiple data sets is performed.

According to an exemplary embodiment of the present invention, the restriction unit is configured to align a scrolling direction and/or display to align a scrolling orientation of one data set to an admissible normal of an another data set out of multiple data sets.

According to an exemplary embodiment of the present invention, the restriction unit is configured to restrict the plurality of admissible display orientations for the at least one of the multiple data sets to the set of restricted display orientations, wherein, if several orientations are admissible, the set of restricted display orientations comprises one orientation with a minimized angle difference to an orientation previously displayed.

According to an exemplary embodiment of the present invention, the restriction unit is configured to restrict the plurality of admissible scrolling directions for the at least one of the multiple data sets to the set of restricted scrolling directions, wherein, if several directions are admissible, the set of restricted scrolling directions comprises one orientation with a minimized angle difference to an direction previously used as scrolling direction.

According to an exemplary embodiment of the present invention, the restriction unit is configured to restrict the plurality of admissible display orientations for the at least one of the multiple data sets to the set of restricted display orientations based on a prior spatial alignment of the data sets; and/or to restrict the plurality of admissible scrolling directions for the at least one of the multiple data sets to the set of restricted scrolling directions based on a prior spatial alignment of the data sets.

A computer program performing the method of the present invention may be stored on a computer-readable medium. A computer-readable medium may be a floppy disk, a hard disk, a CD, a DVD, an USB (Universal Serial Bus) storage device, a RAM (Random Access Memory), a ROM (Read Only Memory) and an EPROM (Erasable Programmable Read Only Memory). A computer-readable medium may also be a data communication network, for example the Internet, which allows downloading a program code.

The methods, systems and devices described herein may be implemented as software in a Digital Signal Processor, DSP, in a micro-controller or in any other side-processor or as hardware circuit within an application specific integrated circuit, ASIC.

The present invention can be implemented in digital electronic circuitry, or in computer hardware, firmware, software, or in combinations thereof, e.g. in available hardware of medical imaging devices or in new hardware dedicated for processing the methods described herein.

A more complete appreciation of the invention and the attendant advantages thereof will be more clearly understood by reference to the following schematic drawings, which are not to scale, wherein.

DETAILED DESCRIPTION OF EMBODIMENTS

The illustration in the drawings is purely schematical and does not intend to provide scaling relations or size information. In different drawings, similar or identical elements are provided with the same reference numerals. Generally, identical parts, units, entities or steps are provided with the same reference symbols in the description.

Figure 1:
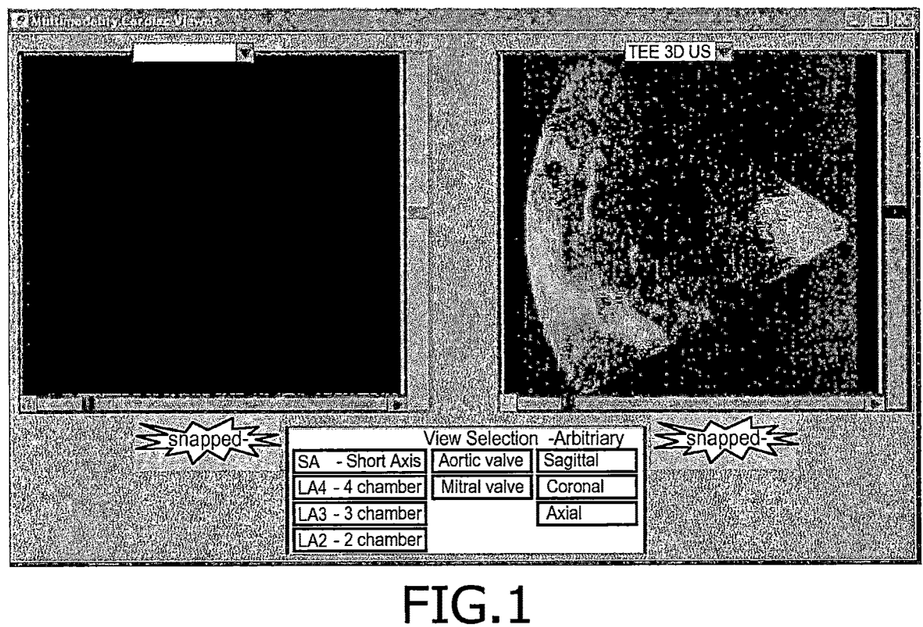
FIG. 1 shows a schematic illustration of a graphical user interface behavior with a three-dimensional data set being displayed for explaining the present invention.

FIG. 1 shows an illustration of a graphical user interface behavior. As so far only a three-dimensional data set is being displayed, which has all orientations admissible, the viewing is still free and arbitrary and oblique views are allowed.

This snapped-orientation viewing principle can be applied in the presence of various limiting dataset types, i.e. for which not all orientations are admissible, such as: a single two-dimensional slice, a multiple two-dimensional (M2D) dataset, a dataset with very anisotropic resolution (e.g. a stack of parallel thick slices). To illustrate, as shown in FIG. 1, we take here the example where the other dataset to be displayed is a pre-aligned three-dimensional volume. In all cases, the scrolling through the simultaneously displayed three-dimensional data is allowed only along the normal to the displayed two-dimensional data plane, showing only reformatted planar cuts parallel to the two-dimensional slice:

Given a single two-dimensional slice, the user is allowed to scroll through the pre-aligned three-dimensional volume only along the normal to the two-dimensional slice plane.

Given a multiple two-dimensional (M2D) dataset, i.e. a set composed of two-dimensional (oblique) slices possibly showing cuts with different orientation through the anatomy, the viewing of a pre-aligned three-dimensional volume is restricted to these two-dimensional slice planes and to scrolling along the normals to these planes. The full three-dimensional linking between the aligned three-dimensional volume and M2D dataset is then highlighted through the sparse admissible views reformatted views in three-dimensional and native views in two-dimensional respectively.

For instance, a cardiac Short-Axis ultrasound data and a 2-chamber Long-Axis ultrasound data together make a dataset that defines a discrete subset of labeled admissible views through a co-displayed three-dimensional volume dataset which may be a three-dimensional ultrasound volume acquired on the same patient possibly at a different time point. In the view selection interface mechanisms, the user is then allowed to select only either the Short-Axis view or the Long-Axis view through the view ports and GUI only these views are enabled, whereas any other labeled view becomes disabled in the view selection panel.

Another example is Cardiac MR where combinations of Short-Axis thick slice stack & several single Long-Axis slices (typically 2-chamber, 4-chamber, 3-chamber, or less typically 6 equi-angled LA slices) may be acquired in certain acquisition protocols like Cine sequences or Late-Enhancement. If a pre-aligned three-dimensional volume is displayed simultaneously, e.g. a three-dimensional US or a CT, then it will be only in the orientations defined by the available Cardiac MR views.

The viewing orientation may also be restricted in the case of very anisotropic resolution (e.g. in-slice resolution much finer than resolution across slices). This is the case for instance in a M2D Short-Axis stack (e.g. in Cine MR sequences, or Late-Enhanced MR), where a set of several thick slices share the same normal. In that case, oblique re-sampling makes little sense for clinical viewing (other than e.g. for a quality assurance check that there's no big misalignment issues between consecutive slices due to motion artifacts across multiple breathholds). Thus the viewing and scrolling can be restricted to only planes orthogonal to that shared normal common to the stacked slices, i.e. planes parallel to the stacked slices.

This restrictive viewing mode implies that, if the GUI includes a labeled view selection mechanism, the excluded views become disabled, e.g. corresponding buttons or drop down menu items become grayed out and inactive.

There may be a visual sign in the GUI that the snapped mode is currently being active, and/or a switch. If the user wants to scroll through the three-dimensional volume along any arbitrary orientation, they may have to explicitly turn off the snapped-orientation viewing mode (or the underlying dataset alignment), and/or switch to a different viewing mode.

We here describe an example of technical usage workflow of one embodiment, in the context of a cardiac image viewer allowing not only the selection of, but also first the recognition of aligned standard labeled views for display:

A cardiac three-dimensional dataset (e.g. CT) is loaded in the viewer.

Standard views are identified:
e.g. Model-based segmentation of the three-dimensional volume is performed using a model in which standard views were encoded;
or views may be defined by landmarks they go through, using either automatic landmark detection or manual landmark clicking.

A cardiac two-dimensional dataset (e.g. two-dimensional US) is loaded in the viewer.

The type of the cardiac two-dimensional view, i.e. its labeled orientation, is obtained in one of the following ways: it was indicated by the user in the GUI at data importing in the previous step or it is parsed from DICOM tags or it is recognized using view classification algorithms.

The corresponding plane encoded in the model is used for reformatting the three-dimensional data set according to the two-dimensional view.

The snapped-orientation viewing mode described in this invention is then switched on by default: view port functionality is restricted to scrolling perpendicular to the viewing plane.

If the GUI includes a 'Free selection' actuator relying on pre-established linking with a model, which otherwise allows the user to select an arbitrary cut through the anatomy, then the snapped-orientation behavior can control the actuator too by restricting it to the admissible orientations for display.

Figure 2:
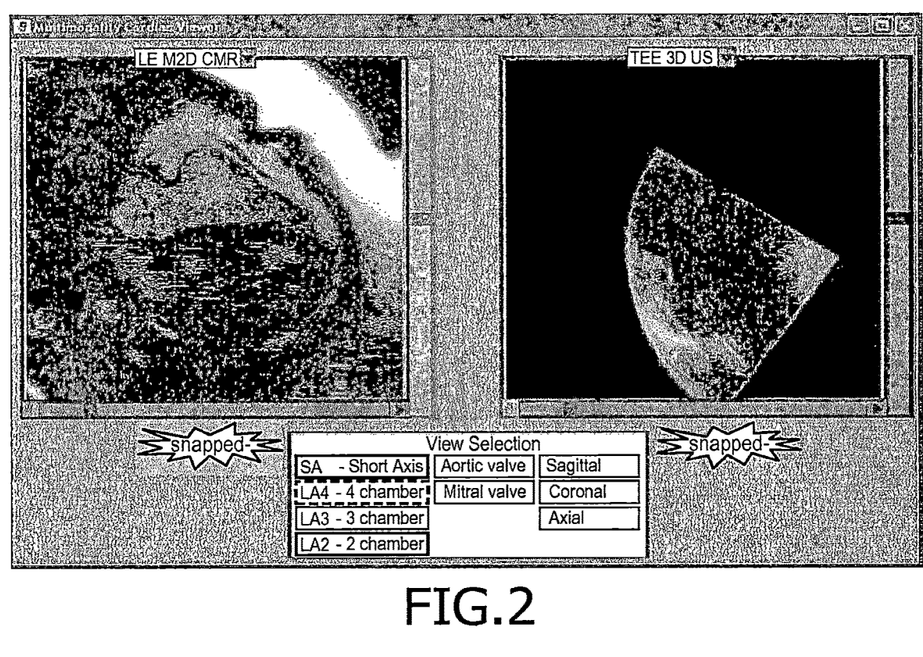
FIG. 2 shows a schematic diagram of a graphical user interface behavior displaying an M2D data set with labeled views for simultaneous aligned display for explaining the present invention.

FIG. 2 shows an illustration of a graphical user interface behavior. The user has selected an M2D data set with labeled use for simultaneous aligned display. Since the data set is limiting, the snapped-orientation viewing mode is automatically switched on, which is highlighted in the graphical user interface. Only the admissible views, as labeled SA, LA4, LA2, remain available for both displayed data sets, and the view of the three-dimensional data set is snapped to the view among those three that are the closest to the previously display view in terms of orientation, namely LA4 here. The user is then allowed to scroll through the three-dimensional data set yet only parallel slices to the LA4 labeled view are shown.

Figure 3:
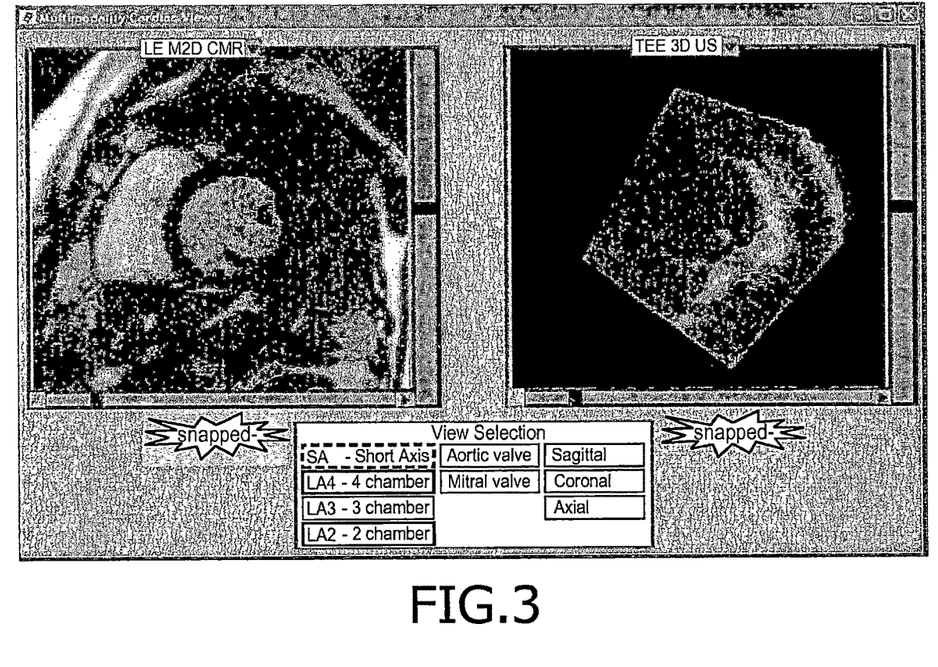
FIG. 3 shows an illustration of a graphical user interface behavior with restricted scrolling for explaining the invention.

FIG. 3 shows an illustration of a graphical user interface behavior, wherein scrolling is not only allowed for the three-dimensional data set but also for the M2D stack of parallel slices.

Figure 4:
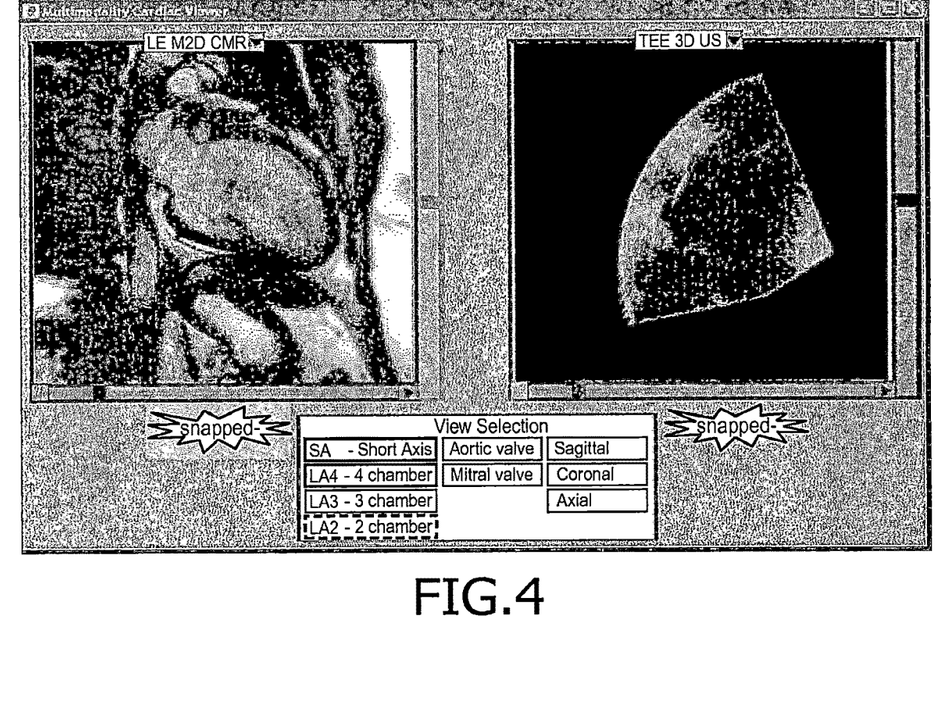
FIG. 4 shows a graphical user interface behavior wherein a user could switch off the snapped mode for explaining the present invention.

FIG. 4 shows an illustration of the graphical user interface behavior. The user could also switch off the snapped mode to be able again to scroll in any arbitrary directions through the three-dimensional data set independently.

Figure 5:
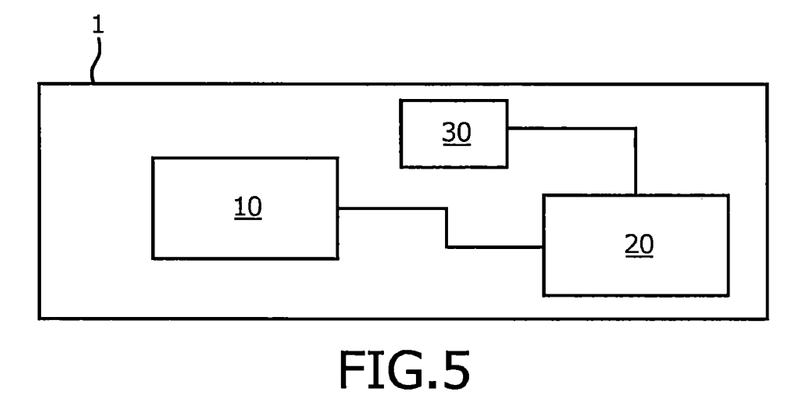
FIG. 5 shows a device for displaying image information according to an exemplary embodiment of the present invention.

FIG. 5 shows a device for displaying image information according to an exemplary embodiment of the present invention.

The device 1 for displaying image information may comprise a detection unit 10, a restriction unit 20, and a display unit 30.

The detection unit 10 may be configured to analyze multiple data sets, which comprise a first data set with a first data set modality and a second data set with a second data set modality, providing analyzed differences of the first data set modality and the second data set modality.

The restriction unit 20 may be configured to restrict a plurality of admissible display orientations for at least one of the multiple data sets to a set of restricted display orientations based on the analyzed differences. Further, the restriction unit 20 may be configured to restrict a plurality of admissible scrolling directions for at least one of the multiple data sets to a set of restricted scrolling directions based on the analyzed differences.

The display unit 30 may be configured to display the multiple data sets using the set of the restricted display orientations and/or the set of restricted scrolling directions.

According to an embodiment of the present invention, for the combined display of a three-dimensional volume dataset and a dataset of two-dimensional slices, or for the combined display of two datasets of two-dimensional slices, where the datasets are pre-aligned in space, a viewing mode is provided which restricts the viewing orientation possibilities for Multi-Planar Reformatting (MPR) of the datasets to only planes parallel to the two-dimensional slice(s). Thus, the orientation possibilities of oblique views of three-dimensional and/or two-dimensional data in space are snapped to a discrete or sparse subset of orientations admissible for all the two-dimensional data displayed simultaneously. In other words, the orientation possibilities of multiple view of at least one of the multiple data sets are restricted to the admissible display orientation in common for all the multiple data sets. The scrolling through three-dimensional data is allowed only along the normal to the displayed two-dimensional data plane. All this holds when one or more datasets are frames belonging to a time sequence.

This snapped-orientation viewing principle can be applied in the presence of various types of limiting datasets, i.e. for which not all orientations are admissible, such as: a single two-dimensional slice, a multiple two-dimensional (M2D) dataset i.e. a set of two-dimensional slices where multiple orientation views may be available, a dataset with very anisotropic resolution (e.g. a stack of two-dimensional slices).

According to an embodiment of the present invention, the restrictive viewing mode may be already natural for the display of slice-based data alone, as no reformatting makes sense. For the simultaneous viewing of multiple datasets, the snapped-orientation viewing mode transfers the restrictiveness due to two-dimensional or slice-based data to the simultaneous display of any three-dimensional volume dataset, which makes sense essentially when the datasets have been aligned beforehand.

According to an embodiment of the present invention, the restrictive viewing mode implies that, if the GUI includes a labeled view selection mechanism, the excluded views become disabled (e.g. corresponding buttons or drop down menu items become grayed out and inactive such as "coronal" or "cardiac Short-Axis"), whereas only the labeled views that are admissible for all displayed datasets remain enabled.

Several extensions are proposed: The snapped-orientation viewing mode may be automatically switched on before loading any dataset and/or as soon as a limiting dataset is selected to be among the datasets displayed. The orientation for immediate display may be selected as the one closest to the last orientation displayed, which can be perceived as an orientation snapping behavior of the viewport (see position snapping below). The snapped-orientation viewing mode can be automatically switched off, e.g. when 2 limiting datasets have incompatible admissible orientations, typically a two-dimensional data set and another two-dimensional data set.

When scrolling parallel slices, a visual sign may highlight that views actually not only match in orientation but also match in actual position or height along the common normal, e.g. frames of a common color may be added around the aligned views to show that they are in full spatial sync. Furthermore, at mode on-switch, the position of the parallel slice for immediate display may be selected as the one closest to the position of the limiting dataset view (and vice versa for an M2D dataset), or just as the position of the parallel slice that goes thru some feature in the last slice displayed, which can be perceived as a position snapping behavior of the viewport.

Figure 6:
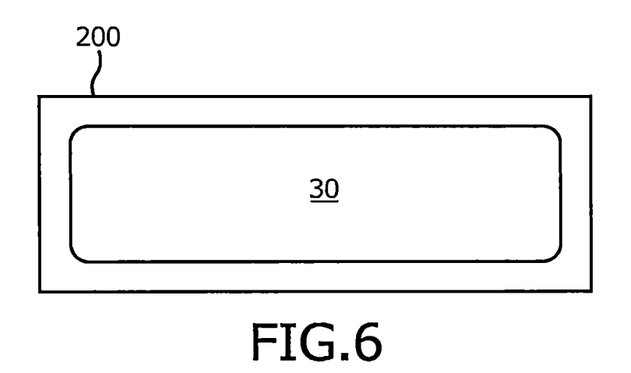
FIG. 6 shows a medical imaging system according to an exemplary embodiment of the present invention.

FIG. 6 shows a medical imaging system according to an exemplary embodiment of the present invention.

A medical imaging system 200 may comprise a device 1 with a display unit 30.

Figure 7:
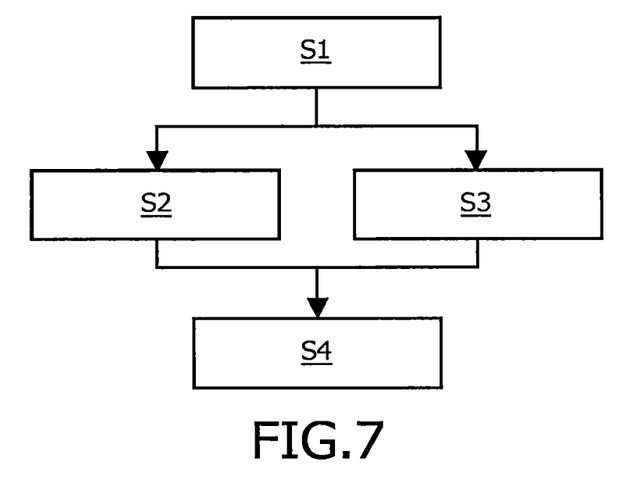
FIG. 7 shows a schematic flow-chart diagram of a method for displaying image information according to an exemplary embodiment of the present invention.

FIG. 7 shows a schematic flow-chart diagram of a method for displaying image information according to an exemplary embodiment of the present invention.

A method for displaying image information, the method may comprise the following steps:

As a first step of the method, identifying S1 a plurality of admissible display orientations of multiple data sets is conducted.

As a further step of the method, restricting S2 the plurality of admissible display orientations of at least one of the multiple data sets to a set of admissible display orientations in common for all the multiple data sets is performed. Simultaneously, in terms of parallel processing, or alternatively or previously or subsequently, restricting S3 a plurality of admissible scrolling directions of at least one of the multiple data sets to a set of scrolling directions that are normal to the restricted admissible display orientations is performed.

As a further step of the method, displaying S4 the multiple data sets using the set of the restricted display orientations and/or the set of restricted scrolling directions is performed.

One possible way in practice to build the snapped-orientation viewing mode concept, and the extensions proposed, is to:
represent orientations associated to datasets by sets of normals and then
manage an intersection of sets of admissible normals and their angles for display, as follows.

For any dataset d loaded into the viewer, a set of associated admissible viewing orientations in space is encoded individually, through the set $N_d$ of three-dimensional unit normal vectors to the admissible viewing orientations. A dataset will be limiting when not all orientations are admissible for its display. For instance:

Given a single two-dimensional slice, the single unit normal $n=\{n_x; n_y; n_z\}$ to its plane shall be stored.

Given a multiple two-dimensional (M2D) dataset, i.e. a set composed of two-dimensional (oblique) slices k possibly showing cuts with different orientation through the anatomy, a collection of the unit normals $n^k=\{n^k_x; n^k_y; n^k_z\}$ to the multiple orientation plane shall be stored, Given a three-dimensional volume dataset, and by default for any given dataset, all orientations shall be admissible, which would be represented by the infinity of all unit normals of the whole unit sphere.

Yet, in the particular case of a given three-dimensional volume dataset with very anisotropic resolution (e.g. a stack of two-dimensional parallel thick slices), where say the z resolution is much less fine than the in-slice x-y resolution by a given ratio threshold, the admissible viewing orientations may be restricted to only x-y slice views, in which case the unit vector of the z axis will be encoded and stored as single unit normal $\{n_x; n_y; n_z\}$.

For the spatial display in the viewer, a set of admissible viewing orientations in space is also encoded, through the set N of three-dimensional unit normal vectors to the admissible viewing orientations.

When 1, 2 (or more) of the loaded datasets are displayed simultaneously, the set N of admissible viewing orientations for display is the subset computed as the intersection of the encoded admissible normal sets of all displayed datasets:

$$N = \bigcap_{displayed\ d} N_d$$

In this process, if a displayed dataset has the full admissibility symbolically encoded, then it brings no restrictiveness to the display. At computing the intersection of admissible orientation views, numerical margins may be tolerated in practical implementation, e.g. an orientation may still be admissible if the corresponding normal vector is within a fixed angle threshold of another admissible normal.

In the snapped-orientation viewing mode, the view possibilities for all datasets displayed are restricted to the set N of admissible viewing orientations.

If some of these orientations are labeled views, e.g. standard views such as "coronal" or "cardiac Short-Axis", which can be selected from the viewer GUI, then only the labeled views that are included in the admissible orientation subset remain enabled for selection, whereas the non-admissible ones become disabled for selection (e.g. corresponding buttons or drop down menu items of the GUI become greyed out and inactive).

Optional automatic mechanisms (extensions) can further be achieved e.g. like follows:

According to an exemplary embodiment of the present invention, viewport snapping behavior is provided: In the event when the snapped-orientation viewing mode is switched on, be it manually or automatically, if several orientations are admissible in N, the orientation for immediate display may be selected as the one closest to the last orientation displayed, i.e. snapped. This translates in terms of the encoded normals as the orientation with the normal minimizing the angle with the normal of the last orientation displayed (or equivalently, e.g. minimizing their sine or their cross-product, or maximizing their cosine or dot product).

$$n_{displayed} = \arg\min_{n_k} \angle(n_k, n_{last}) = \arg\min_{n_k} \|n_k \wedge n_{last}\|$$

According to an exemplary embodiment of the present invention, automatic switch off is provided: If the intersection is empty, then the snapped-orientation viewing mode may be automatically switched off, i.e. the view orientations of the datasets are independent (the viewing orientation of the datasets already displayed before the event may be e.g. left unchanged, or returned to some stored previous state, or again moved to the non-matching orientation that is closest in terms of angle).

According to an exemplary embodiment of the present invention, highlight of full spatial sync is provided: This can be implemented by encoding an origin along the common normal, and a numerical margin on distance between parallel slices may be tolerated.

The snapped orientation viewing principle can be applied in the presence of various limiting data set types, i.e. for which not all orientations are admissible, such as a single two-dimensional slice, a multiple two-dimensional, M2D, data set, a data set with very anisotropic resolution or any further data set.

For all cases, the scrolling through the simultaneously displayed three-dimensional data is allowed only among the normal to the displayed two-dimensional data set of a plane, showing only reformatted planar cuts parallel to the two-dimensional slice:

Given a single two-dimensional slice, the user may be allowed to scroll through the pre-aligned three-dimensional volume only along the normal to the two-dimensional slice plane.

Given a multiple two-dimensional data set, i.e. a set composed of two-dimensional, oblique, slices possibly showing cuts with different orientation through the anatomy, the viewing of the pre-aligned three-dimensional volume is restricted to these two-dimensional slice planes and to scrolling along the normals to these planes. The full three-dimensional linking between the aligned three-dimensional volume and the M2D data set is then highlighted through the sparse admissible views and reformatted views in three-dimensional and native views in two-dimensional, respectively.

For instance, a cardiac short axis ultrasound data and a two chamber long axis ultrasound data together make a data set that defines a discrete subset of labeled admissible views through a co-displayed three-dimensional volume data set which may be a three-dimensional ultrasound volume acquired on the same patient. The data sets may be acquired at different time points. In the view selection interface mechanisms, the user is then allowed to select only either the short axis view or the long-axis view through the viewports and the graphical user interface.

Thereby, any other labeled view becomes disabled in the view selection panel.

A further example may be given by cardiac MR, where combinations of short-axis thick slice stack and several single long-axis slices, typically two chamber, four chamber, three chamber or further slices, may be acquired in certain acquisition protocols like cine sequences or late-enhancement.

If a pre-aligned three-dimensional volume is displayed simultaneously, e.g. a three-dimensional Ultrasound, US, or a CT, then it will be only in the orientations defined by the available cardiac MR views.

The viewing orientation may also be restricted in the case of very anisotropic resolution. This may be the case for instance in a M2D short-axis stack. Therefore, the viewing and scrolling can be restricted to only planes orthogonal to that shared normal common to the stacked slice, i.e. planes parallel to the stacked slice.

It has to be noted that embodiments of the invention are described with reference to different subject-matters. In particular, some embodiments are described with reference to method type claims whereas other embodiments are described with reference to the device type claims.

However, a person skilled in the art will gather from the above and the following description that, unless otherwise notified, in addition to any combination of features belonging to one type of subject-matter also any combination between features relating to different subject-matters is considered to be disclosed with this application.

However, all features can be combined providing synergetic effects that are more than the simple summation of the features.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality.

The invention claimed is:

1. A device for displaying image information, the device comprising:
    a detection unit configured to,
        analyze multiple data including a first data set with a first data set modality and a second data set with a second data set modality, wherein the first data set has a first dimensionality and the second data set has a second dimensionality and the first and second dimensionalities are different, providing analyzed differences of the first data set modality and the second data set modality, and
        identify a plurality of admissible display orientations of multiple data sets;
    a restriction unit configured to,
        restrict the plurality of admissible display orientations of at least one of the multiple data sets to a set of restricted display orientations in common for all the multiple data sets based on the analyzed differences, wherein a restrictive mode enables selected views admissible for the at least one multiple data set and disables excluded views for the at least one multiple data set, and
        restrict a plurality of admissible scrolling directions of at least one of the multiple data sets to a set of restricted scrolling directions that are normal to the restricted admissible display orientations; and
    a display unit configured to display the multiple data sets using the set of the restricted display orientations and the set of restricted scrolling directions.

2. The device according to claim 1, wherein the first data set is a three-dimensional data set and the second data set is a two-dimensional data set.

3. The device according to claim 2, wherein the restriction unit is configured to restrict the plurality of admissible display orientations for the first data set to the set of restricted display orientations, which are planes parallel to the two-dimensional second data set.

4. The device according to claim 2, wherein the restriction unit is configured to restrict the plurality of admissible scrolling directions for the first data set to the set of restricted scrolling directions, which are normal to displayable planes of the two-dimensional second data set.

5. The device according to claim 1, wherein the detection unit is configured to identify the plurality of admissible display orientations using view classification procedures or using user input.

6. The device according to claim 1, wherein the restriction unit is configured to restrict the plurality of admissible display orientations and/or the plurality of admissible scrolling directions during a viewing mode of the device.

7. The device according to claim 1, wherein the restriction unit is configured to restrict the plurality of admissible display orientations for at least one of the multiple data sets to the set of restricted display orientations within a fixed angle threshold of an admissible normal.

8. The device according to claim 1, wherein the restriction unit is configured to restrict the plurality of admissible scrolling directions for at least one of the multiple data sets to the set of restricted scrolling directions within a fixed angle threshold of an admissible normal.

9. The device according to claim 1, wherein the restriction unit is configured to restrict the plurality of admissible display orientations for the at least one of the multiple data sets to the set of restricted display orientations, wherein, if several orientations are admissible, the set of restricted display orientations comprises one orientation with a minimized angle difference to an orientation previously displayed.

10. The device according to claim 1, wherein the restriction unit is configured to restrict the plurality of admissible scrolling directions for the at least one of the multiple data sets to the set of restricted scrolling directions, wherein, if several directions are admissible, the set of restricted scrolling directions comprises one orientation with a minimized angle difference to an direction previously used as scrolling direction.

11. The device according to claim 1, wherein the display unit is configured to display a position matching of the multiple data sets, when the multiple data sets are displayed by the display unit and a scrolling at least through one of the multiple data sets is performed.

12. The device according to claim 1, wherein the restriction unit is configured to restrict the plurality of admissible display orientations for the at least one of the multiple data sets to the set of restricted display orientations based on a prior spatial alignment of the data sets; and/or to restrict the plurality of admissible scrolling directions for the at least one of the multiple data sets to the set of restricted scrolling directions based on a prior spatial alignment of the data sets.

13. A medical imaging system comprising a device according to claim 1.

14. A method for displaying image information, the method comprising the steps of:
    analyzing multiple data sets including a first data set with a first data set modality and a second data set with a second data set modality, wherein the first data set has a first dimensionality and the second data set has a second dimensionality and the first and second dimensionalities are different, to provide analyzed differences of the first data set modality and the second data set modality;
    identifying a plurality of admissible display orientations of multiple data sets;
    restricting the plurality of admissible display orientations of at least one of the multiple data sets to a set of admissible display orientations in common for all the multiple data sets based on the analyzed differences, wherein a restrictive mode enables selected views admissible for the at least one multiple data set and disables excluded views for the at least one multiple data set;

restricting a plurality of admissible scrolling directions of at least one of the multiple data sets to a set of scrolling directions that are normal to the restricted admissible display orientations; and displaying the multiple data sets using the set of the restricted display orientations and/or the set of restricted scrolling directions.

15. A non-transitory computer readable medium storing a computer program that is executable by a processor, the computer program comprising instructions, when executed by the processor, causing the processor to perform the method according to claim 14.

\* \* \* \* \*